United States Patent
Armstrong et al.

(10) Patent No.: US 7,869,867 B2
(45) Date of Patent: Jan. 11, 2011

(54) IMPLANTABLE NEUROSTIMULATOR WITH REFRACTORY STIMULATION

(75) Inventors: Scott A. Armstrong, Danbury, TX (US); Randolph K. Armstrong, Houston, TX (US)

(73) Assignee: Cyberonics, Inc., Houston, TX (US)

( * ) Notice: Subject to any disclaimer, the term of this patent is extended or adjusted under 35 U.S.C. 154(b) by 708 days.

(21) Appl. No.: 11/588,512

(22) Filed: Oct. 27, 2006

(65) Prior Publication Data

US 2008/0103532 A1 May 1, 2008

(51) Int. Cl.
*A61N 1/00* (2006.01)
(52) U.S. Cl. .......................................................... 607/2
(58) Field of Classification Search ................... 607/67, 607/66, 72, 70, 118, 2, 5, 7, 9, 18, 55, 57, 607/45–48; 600/509, 515, 545
See application file for complete search history.

(56) References Cited

U.S. PATENT DOCUMENTS

| | | | |
|---|---|---|---|
| 3,760,812 A | 9/1973 | Timm et al. | |
| 3,796,221 A | 3/1974 | Hagfors | |
| 4,107,469 A | 8/1978 | Jenkins | |
| 4,305,402 A | 12/1981 | Katims | |
| 4,338,945 A | 7/1982 | Kosugi et al. | |
| 4,424,812 A | 1/1984 | Lesnick | |
| 4,431,000 A | 2/1984 | Butler et al. | |
| 4,459,989 A | 7/1984 | Borkan | |
| 4,503,863 A | 3/1985 | Katims | |
| 4,541,432 A | 9/1985 | Molina-Negro et al. | |
| 4,573,481 A | 3/1986 | Bullara | |
| 4,577,316 A | 3/1986 | Schiff | |
| 4,590,946 A | 5/1986 | Loeb | |
| 4,592,339 A | 6/1986 | Kuzmak et al. | |
| 4,606,349 A | 8/1986 | Livingston et al. | |
| 4,608,985 A | 9/1986 | Crish et al. | |
| 4,612,934 A | 9/1986 | Borkan | |
| 4,625,308 A | 11/1986 | Kim et al. | |
| 4,628,942 A | 12/1986 | Sweeney et al. | |
| 4,640,286 A * | 2/1987 | Thomson ..................... | 607/70 |

(Continued)

FOREIGN PATENT DOCUMENTS

CA 2339971 6/2004

(Continued)

OTHER PUBLICATIONS

Bachman, D.,S. et al.; "Effect of Vagal Alloys and Serotonin on Units of Cingulate Cortex in Monkeys;" Brain Research, vol. 130 (1977). pp. 253-269.

(Continued)

*Primary Examiner*—George Manuel
*Assistant Examiner*—Robert N Wieland
(74) *Attorney, Agent, or Firm*—Conley Rose, P.C.; Timothy L. Scott; Darrell N. Fuller (57) ABSTRACT

In some embodiments, a method comprises providing an electrical signal to a nerve to evoke an action potential. The nerve thereby enters a refractory period in which the nerve is in a refractory state. The method further comprises, during the refractory period, providing an electrical signal to the nerve thereby altering the refractory period of the nerve or non-target tissues.

23 Claims, 3 Drawing Sheets

U.S. PATENT DOCUMENTS

| | | | |
|---|---|---|---|
| 4,649,936 A | 3/1987 | Ungar et al. |
| 4,702,254 A | 10/1987 | Zabara |
| 4,793,353 A | 12/1988 | Borkan |
| 4,867,164 A | 9/1989 | Zabara |
| 4,920,979 A | 5/1990 | Bullara |
| 4,949,721 A | 8/1990 | Toriu et al. |
| 4,977,895 A | 12/1990 | Tannenbaum |
| 5,025,807 A | 6/1991 | Zabara |
| 5,081,987 A | 1/1992 | Nigam |
| 5,154,172 A | 10/1992 | Terry, Jr. et al. |
| 5,179,950 A | 1/1993 | Stanislaw |
| 5,186,170 A | 2/1993 | Varrichio et al. |
| 5,188,104 A | 2/1993 | Wernicke et al. |
| 5,205,285 A | 4/1993 | Baker, Jr. |
| 5,215,086 A | 6/1993 | Terry, Jr. et al. |
| 5,222,494 A | 6/1993 | Baker, Jr. |
| 5,231,988 A | 8/1993 | Wernicke et al. |
| 5,235,980 A | 8/1993 | Varrichio et al. |
| 5,263,480 A | 11/1993 | Wernicke et al. |
| 5,269,303 A | 12/1993 | Wernicke et al. |
| 5,299,569 A | 4/1994 | Wernicke et al. |
| 5,330,507 A | 7/1994 | Schwartz |
| 5,330,515 A | 7/1994 | Rutecki et al. |
| 5,334,221 A | 8/1994 | Bardy |
| 5,354,320 A | 10/1994 | Schaldach et al. |
| 5,411,531 A | 5/1995 | Hill et al. |
| 5,411,540 A | 5/1995 | Edell et al. |
| 5,423,872 A | 6/1995 | Cigaina |
| 5,507,784 A | 4/1996 | Hill et al. |
| 5,522,862 A | 6/1996 | Testerman et al. |
| 5,522,865 A | 6/1996 | Schulman et al. |
| 5,540,730 A | 7/1996 | Terry, Jr. et al. |
| 5,540,734 A | 7/1996 | Zabara |
| 5,571,150 A | 11/1996 | Wernicke et al. |
| 5,601,617 A | 2/1997 | Loeb et al. |
| 5,611,350 A | 3/1997 | John |
| 5,620,468 A * | 4/1997 | Mongeon et al. ............. 607/5 |
| 5,645,570 A | 7/1997 | Corbucci |
| 5,651,378 A | 7/1997 | Matheny et al. |
| 5,658,318 A | 8/1997 | Stroetmann et al. |
| 5,690,681 A | 11/1997 | Geddes et al. |
| 5,690,688 A | 11/1997 | Noren et al. |
| 5,690,691 A | 11/1997 | Chen et al. |
| 5,700,282 A | 12/1997 | Zabara |
| 5,702,428 A | 12/1997 | Tippey et al. |
| 5,702,429 A | 12/1997 | King |
| 5,707,400 A | 1/1998 | Terry, Jr. et al. |
| 5,755,750 A | 5/1998 | Petruska et al. |
| 5,792,212 A | 8/1998 | Weijand |
| 5,800,474 A | 9/1998 | Benabid et al. |
| 5,814,092 A | 9/1998 | King |
| 5,836,994 A | 11/1998 | Bourgeois |
| 5,861,014 A | 1/1999 | Familoni |
| 5,871,505 A * | 2/1999 | Adams et al. .................. 607/5 |
| 5,913,882 A | 6/1999 | King |
| 5,916,239 A | 6/1999 | Geddes et al. |
| 5,928,272 A | 7/1999 | Adkins et al. |
| 5,941,906 A | 8/1999 | Barreras, Sr. et al. |
| 5,995,868 A | 11/1999 | Osorio et al. |
| 6,002,966 A | 12/1999 | Loeb et al. |
| 6,016,449 A | 1/2000 | Fischell et al. |
| 6,041,258 A | 3/2000 | Cigaina et al. |
| 6,083,249 A | 7/2000 | Familoni |
| 6,101,412 A | 8/2000 | Duhaylongsod |
| 6,104,955 A | 8/2000 | Bourgeois |
| 6,104,956 A | 8/2000 | Naritoku et al. |
| 6,115,628 A | 9/2000 | Stadler et al. |
| 6,132,361 A | 10/2000 | Epstein et al. |
| 6,141,590 A | 10/2000 | Renirie et al. |
| 6,161,044 A | 12/2000 | Silverstone |
| 6,167,311 A | 12/2000 | Rezai |
| 6,175,764 B1 | 1/2001 | Loeb et al. |
| 6,188,929 B1 | 2/2001 | Giordano |
| 6,219,580 B1 | 4/2001 | Faltys et al. |
| 6,221,908 B1 | 4/2001 | Kilgard et al. |
| 6,238,423 B1 | 5/2001 | Bardy |
| 6,249,704 B1 | 6/2001 | Maltan et al. |
| 6,253,109 B1 | 6/2001 | Gielen |
| 6,266,564 B1 | 7/2001 | Hill et al. |
| 6,269,270 B1 | 7/2001 | Boveja |
| 6,295,472 B1 | 9/2001 | Rubinstein et al. |
| 6,304,775 B1 | 10/2001 | Iasemidis et al. |
| 6,308,102 B1 | 10/2001 | Sieracki |
| 6,324,421 B1 | 11/2001 | Stadler et al. |
| 6,327,503 B1 | 12/2001 | Familoni |
| 6,339,725 B1 | 1/2002 | Naritoku et al. |
| 6,341,236 B1 | 1/2002 | Osorio et al. |
| 6,353,762 B1 | 3/2002 | Baudino et al. |
| 6,356,788 B2 | 3/2002 | Boveja |
| 6,358,203 B2 | 3/2002 | Bardy |
| 6,366,813 B1 | 4/2002 | DiLorenzo |
| 6,366,814 B1 | 4/2002 | Boveja |
| 6,374,140 B1 | 4/2002 | Rise |
| 6,381,493 B1 | 4/2002 | Stadler et al. |
| 6,381,496 B1 | 4/2002 | Meadows et al. |
| 6,381,499 B1 | 4/2002 | Taylor et al. |
| 6,418,344 B1 | 7/2002 | Rezai et al. |
| 6,425,852 B1 | 7/2002 | Epstein et al. |
| 6,438,423 B1 | 8/2002 | Rezai et al. |
| 6,449,512 B1 | 9/2002 | Boveja |
| 6,453,199 B1 | 9/2002 | Kobozev |
| 6,459,936 B2 | 10/2002 | Fischell et al. |
| 6,463,328 B1 | 10/2002 | John |
| 6,466,822 B1 | 10/2002 | Pless |
| 6,473,639 B1 | 10/2002 | Fischell et al. |
| 6,473,644 B1 | 10/2002 | Terry, Jr. et al. |
| 6,477,417 B1 | 11/2002 | Levine |
| 6,477,418 B2 | 11/2002 | Plicchi et al. |
| 6,480,743 B1 | 11/2002 | Kirkpatrick et al. |
| 6,484,132 B1 | 11/2002 | Hively et al. |
| 6,487,446 B1 | 11/2002 | Hill et al. |
| 6,505,074 B2 | 1/2003 | Boveja et al. |
| 6,522,928 B2 | 2/2003 | Whitehurst et al. |
| 6,532,388 B1 | 3/2003 | Hill et al. |
| 6,549,804 B1 | 4/2003 | Osorio et al. |
| 6,556,868 B2 | 4/2003 | Naritoku et al. |
| 6,564,102 B1 | 5/2003 | Boveja |
| 6,565,503 B2 | 5/2003 | Leysieffer et al. |
| 6,579,280 B1 | 6/2003 | Kovach et al. |
| 6,587,719 B1 | 7/2003 | Barrett et al. |
| 6,587,724 B2 | 7/2003 | Mann |
| 6,587,726 B2 | 7/2003 | Lurie et al. |
| 6,587,727 B2 | 7/2003 | Osorio et al. |
| 6,591,138 B1 | 7/2003 | Fischell et al. |
| 6,594,524 B2 | 7/2003 | Esteller et al. |
| 6,600,953 B2 | 7/2003 | Flesler et al. |
| 6,609,025 B2 | 8/2003 | Barrett et al. |
| 6,609,030 B1 | 8/2003 | Rezai et al. |
| 6,609,031 B1 | 8/2003 | Law et al. |
| 6,610,713 B2 | 8/2003 | Tracey |
| 6,611,715 B1 | 8/2003 | Boveja |
| 6,612,983 B1 | 9/2003 | Marchal |
| 6,615,081 B1 | 9/2003 | Boveja |
| 6,615,084 B1 | 9/2003 | Cigaina |
| 6,615,085 B1 | 9/2003 | Boveja |
| 6,622,038 B2 | 9/2003 | Barrett et al. |
| 6,622,041 B2 | 9/2003 | Terry, Jr. et al. |
| 6,622,047 B2 | 9/2003 | Barrett et al. |
| 6,628,987 B1 | 9/2003 | Hill et al. |
| 6,656,960 B2 | 12/2003 | Puskas |
| 6,662,053 B2 | 12/2003 | Borkan |
| 6,668,191 B1 | 12/2003 | Boveja |
| 6,671,547 B2 | 12/2003 | Lyster et al. |
| 6,671,555 B2 | 12/2003 | Gielen et al. |

| | | |
|---|---|---|
| 6,671,556 B2 | 12/2003 | Osorio et al. |
| 6,684,104 B2 | 1/2004 | Gordon et al. |
| 6,684,105 B2 | 1/2004 | Cohen et al. |
| 6,690,973 B2 | 2/2004 | Hill et al. |
| 6,690,974 B2 | 2/2004 | Archer et al. |
| 6,701,187 B1 * | 3/2004 | Bornzin et al. ............... 607/14 |
| 6,708,064 B2 | 3/2004 | Rezai |
| 6,721,603 B2 | 4/2004 | Zabara et al. |
| 6,731,979 B2 | 5/2004 | MacDonald |
| 6,731,986 B2 | 5/2004 | Mann |
| 6,754,536 B2 | 6/2004 | Swoyer et al. |
| 6,760,626 B1 | 7/2004 | Boveja |
| 6,764,498 B2 | 7/2004 | Mische |
| 6,768,969 B1 | 7/2004 | Nikitin et al. |
| 6,775,573 B2 | 8/2004 | Schuler et al. |
| 6,793,670 B2 | 9/2004 | Osorio et al. |
| 6,819,956 B2 | 11/2004 | DiLorenzo |
| 6,826,428 B1 | 11/2004 | Chen et al. |
| 6,832,114 B1 | 12/2004 | Whitehurst et al. |
| 6,853,862 B1 | 2/2005 | Marchal et al. |
| 6,885,888 B2 | 4/2005 | Rezai |
| 6,895,278 B1 | 5/2005 | Gordon |
| 6,904,390 B2 | 6/2005 | Nikitin et al. |
| 6,907,295 B2 | 6/2005 | Gross et al. |
| 6,920,357 B2 | 7/2005 | Osorio et al. |
| 6,934,580 B1 | 8/2005 | Osorio et al. |
| 6,944,501 B1 | 9/2005 | Pless |
| 6,944,503 B2 * | 9/2005 | Crowe et al. ............... 607/66 |
| 6,961,618 B2 | 11/2005 | Osorio et al. |
| 7,006,859 B1 | 2/2006 | Osorio et al. |
| 7,006,872 B2 | 2/2006 | Gielen et al. |
| 7,050,856 B2 | 5/2006 | Stypulkowski |
| 7,054,686 B2 | 5/2006 | MacDonald |
| 7,146,217 B2 | 12/2006 | Firlik et al. |
| 7,167,750 B2 | 1/2007 | Knudson et al. |
| 7,177,678 B1 | 2/2007 | Osorio et al. |
| 7,188,053 B2 | 3/2007 | Nikitin et al. |
| 7,204,833 B1 | 4/2007 | Osorio et al. |
| 7,209,787 B2 | 4/2007 | DiLorenzo |
| 7,231,254 B2 | 6/2007 | DiLorenzo |
| 7,236,830 B2 | 6/2007 | Gliner |
| 7,236,831 B2 | 6/2007 | Firlik et al. |
| 7,242,983 B2 | 7/2007 | Frei et al. |
| 7,242,984 B2 | 7/2007 | DiLorenzo |
| 7,340,302 B1 | 3/2008 | Falkenberg et al. |
| 2001/0034541 A1 | 10/2001 | Lyden |
| 2001/0037220 A1 | 11/2001 | Merry et al. |
| 2002/0052539 A1 | 5/2002 | Haller et al. |
| 2002/0065509 A1 | 5/2002 | Lebel et al. |
| 2002/0072782 A1 | 6/2002 | Osorio et al. |
| 2002/0082480 A1 | 6/2002 | Riff et al. |
| 2002/0099412 A1 | 7/2002 | Fischell et al. |
| 2002/0099417 A1 | 7/2002 | Naritoku et al. |
| 2002/0116030 A1 | 8/2002 | Rezai |
| 2002/0120310 A1 | 8/2002 | Linden et al. |
| 2002/0133204 A1 | 9/2002 | Hrdlicka |
| 2002/0143368 A1 | 10/2002 | Bakels et al. |
| 2002/0151939 A1 | 10/2002 | Rezai |
| 2002/0153901 A1 | 10/2002 | Davis et al. |
| 2002/0188214 A1 | 12/2002 | Misczynski et al. |
| 2003/0028226 A1 | 2/2003 | Thompson et al. |
| 2003/0055457 A1 | 3/2003 | MacDonald |
| 2003/0074032 A1 | 4/2003 | Gliner |
| 2003/0083716 A1 | 5/2003 | Nicolelis et al. |
| 2003/0083727 A1 * | 5/2003 | Casavant et al. ............ 607/122 |
| 2003/0088274 A1 | 5/2003 | Gliner et al. |
| 2003/0095648 A1 | 5/2003 | Kaib et al. |
| 2003/0097161 A1 | 5/2003 | Firlik et al. |
| 2003/0109903 A1 | 6/2003 | Berrang et al. |
| 2003/0125786 A1 | 7/2003 | Gliner et al. |
| 2003/0130706 A1 | 7/2003 | Sheffield et al. |
| 2003/0144711 A1 | 7/2003 | Pless et al. |
| 2003/0144829 A1 | 7/2003 | Geatz et al. |
| 2003/0181954 A1 | 9/2003 | Rezai |
| 2003/0181958 A1 | 9/2003 | Dobak |
| 2003/0181959 A1 | 9/2003 | Dobak |
| 2003/0208212 A1 | 11/2003 | Cigaina |
| 2003/0210147 A1 | 11/2003 | Humbard |
| 2003/0212440 A1 | 11/2003 | Boveja |
| 2003/0236558 A1 | 12/2003 | Whitehurst et al. |
| 2004/0006278 A1 | 1/2004 | Webb et al. |
| 2004/0015205 A1 | 1/2004 | Whitehurst et al. |
| 2004/0036377 A1 | 2/2004 | Mezinis |
| 2004/0039424 A1 | 2/2004 | Merritt et al. |
| 2004/0088024 A1 | 5/2004 | Firlik et al. |
| 2004/0102811 A1 * | 5/2004 | Schwartz et al. ............... 607/5 |
| 2004/0111139 A1 | 6/2004 | McCreery |
| 2004/0112894 A1 | 6/2004 | Varma |
| 2004/0122484 A1 | 6/2004 | Hatlestad et al. |
| 2004/0122485 A1 | 6/2004 | Stahmann et al. |
| 2004/0122489 A1 | 6/2004 | Mazar et al. |
| 2004/0133119 A1 | 7/2004 | Osorio et al. |
| 2004/0138516 A1 | 7/2004 | Osorio et al. |
| 2004/0138517 A1 | 7/2004 | Osorio et al. |
| 2004/0138518 A1 | 7/2004 | Rise et al. |
| 2004/0138647 A1 | 7/2004 | Osorio et al. |
| 2004/0138711 A1 | 7/2004 | Osorio et al. |
| 2004/0147969 A1 | 7/2004 | Mann et al. |
| 2004/0147992 A1 | 7/2004 | Bluger et al. |
| 2004/0153129 A1 | 8/2004 | Pless et al. |
| 2004/0158119 A1 | 8/2004 | Osorio et al. |
| 2004/0158165 A1 | 8/2004 | Yonce et al. |
| 2004/0167583 A1 | 8/2004 | Knudson et al. |
| 2004/0167587 A1 | 8/2004 | Thompson |
| 2004/0172085 A1 | 9/2004 | Knudson et al. |
| 2004/0172088 A1 | 9/2004 | Knudson et al. |
| 2004/0172089 A1 | 9/2004 | Whitehurst et al. |
| 2004/0172091 A1 | 9/2004 | Rezai |
| 2004/0172094 A1 | 9/2004 | Cohen et al. |
| 2004/0176812 A1 | 9/2004 | Knudson et al. |
| 2004/0176831 A1 | 9/2004 | Gliner et al. |
| 2004/0193231 A1 | 9/2004 | David et al. |
| 2004/0199146 A1 | 10/2004 | Rogers et al. |
| 2004/0199187 A1 | 10/2004 | Loughran |
| 2004/0199212 A1 | 10/2004 | Fischell et al. |
| 2004/0210270 A1 | 10/2004 | Erickson |
| 2004/0210274 A1 | 10/2004 | Bauhahn et al. |
| 2004/0249302 A1 | 12/2004 | Donoghue et al. |
| 2004/0249416 A1 | 12/2004 | Yun et al. |
| 2004/0260346 A1 | 12/2004 | Overall et al. |
| 2004/0263172 A1 | 12/2004 | Gray et al. |
| 2005/0004615 A1 | 1/2005 | Sanders |
| 2005/0004621 A1 | 1/2005 | Boveja et al. |
| 2005/0010262 A1 | 1/2005 | Rezai et al. |
| 2005/0015128 A1 | 1/2005 | Rezai et al. |
| 2005/0016657 A1 | 1/2005 | Bluger |
| 2005/0020887 A1 | 1/2005 | Goldberg |
| 2005/0021092 A1 | 1/2005 | Yun et al. |
| 2005/0021103 A1 | 1/2005 | DiLorenzo |
| 2005/0021104 A1 | 1/2005 | DiLorenzo |
| 2005/0021105 A1 | 1/2005 | Firlik et al. |
| 2005/0021106 A1 | 1/2005 | Firlik et al. |
| 2005/0021107 A1 | 1/2005 | Firlik et al. |
| 2005/0021118 A1 | 1/2005 | Genau et al. |
| 2005/0027284 A1 | 2/2005 | Lozano et al. |
| 2005/0028026 A1 | 2/2005 | Shirley et al. |
| 2005/0033378 A1 | 2/2005 | Sheffield et al. |
| 2005/0033379 A1 | 2/2005 | Lozano et al. |
| 2005/0038326 A1 | 2/2005 | Mathur |
| 2005/0038484 A1 | 2/2005 | Knudson et al. |
| 2005/0049515 A1 | 3/2005 | Misczynski et al. |
| 2005/0049655 A1 | 3/2005 | Boveja et al. |
| 2005/0060007 A1 | 3/2005 | Goetz |
| 2005/0060008 A1 | 3/2005 | Goetz |
| 2005/0060009 A1 | 3/2005 | Goetz |
| 2005/0060010 A1 | 3/2005 | Goetz |

| | | |
|---|---|---|
| 2005/0065562 A1 | 3/2005 | Rezai |
| 2005/0065573 A1 | 3/2005 | Rezai |
| 2005/0065574 A1 | 3/2005 | Rezai |
| 2005/0065575 A1 | 3/2005 | Dobak |
| 2005/0070971 A1 | 3/2005 | Fowler et al. |
| 2005/0075679 A1 | 4/2005 | Gliner et al. |
| 2005/0075680 A1 | 4/2005 | Lowry et al. |
| 2005/0075681 A1 | 4/2005 | Rezai et al. |
| 2005/0075691 A1 | 4/2005 | Phillips et al. |
| 2005/0075701 A1 | 4/2005 | Shafer |
| 2005/0075702 A1 | 4/2005 | Shafer |
| 2005/0088145 A1 | 4/2005 | Loch |
| 2005/0101873 A1 | 5/2005 | Misczynski et al. |
| 2005/0102002 A1 | 5/2005 | Salo et al. |
| 2005/0107753 A1 | 5/2005 | Rezai et al. |
| 2005/0107842 A1 | 5/2005 | Rezai |
| 2005/0107858 A1 | 5/2005 | Bulger |
| 2005/0113705 A1 | 5/2005 | Fischell et al. |
| 2005/0113744 A1 | 5/2005 | Donoghue et al. |
| 2005/0119703 A1 | 6/2005 | DiLorenzo |
| 2005/0124901 A1 | 6/2005 | Misczynski et al. |
| 2005/0131467 A1 | 6/2005 | Boveja et al. |
| 2005/0131485 A1 | 6/2005 | Knudson et al. |
| 2005/0131486 A1 | 6/2005 | Boveja et al. |
| 2005/0131493 A1 | 6/2005 | Boveja et al. |
| 2005/0131506 A1 | 6/2005 | Rezai et al. |
| 2005/0137480 A1 | 6/2005 | Alt et al. |
| 2005/0143781 A1 | 6/2005 | Carbunaru et al. |
| 2005/0143786 A1 | 6/2005 | Boveja et al. |
| 2005/0148893 A1 | 7/2005 | Misczynski et al. |
| 2005/0148894 A1 | 7/2005 | Misczynski et al. |
| 2005/0148895 A1 | 7/2005 | Misczynski et al. |
| 2005/0153885 A1 | 7/2005 | Yun et al. |
| 2005/0154425 A1 | 7/2005 | Boveja et al. |
| 2005/0154435 A1 | 7/2005 | Stern et al. |
| 2005/0159789 A1 | 7/2005 | Brockway et al. |
| 2005/0161052 A1 | 7/2005 | Rezai et al. |
| 2005/0165458 A1 | 7/2005 | Boveja et al. |
| 2005/0177192 A1 | 8/2005 | Rezai et al. |
| 2005/0177200 A1 | 8/2005 | George et al. |
| 2005/0177206 A1 | 8/2005 | North et al. |
| 2005/0182389 A1 | 8/2005 | LaPorte et al. |
| 2005/0187590 A1 | 8/2005 | Boveja et al. |
| 2005/0187593 A1 | 8/2005 | Housworth et al. |
| 2005/0187796 A1 | 8/2005 | Rosenfeld et al. |
| 2005/0192644 A1 | 9/2005 | Boveja et al. |
| 2005/0197590 A1 | 9/2005 | Osorio et al. |
| 2005/0222631 A1 | 10/2005 | Dalal et al. |
| 2005/0228693 A1 | 10/2005 | Webb et al. |
| 2005/0240246 A1 | 10/2005 | Lee et al. |
| 2005/0245944 A1 | 11/2005 | Rezai |
| 2005/0245971 A1 | 11/2005 | Brockway et al. |
| 2005/0245990 A1 | 11/2005 | Roberson |
| 2005/0261542 A1 | 11/2005 | Riehl |
| 2005/0267550 A1 | 12/2005 | Hess et al. |
| 2005/0272280 A1 | 12/2005 | Osypka |
| 2005/0277872 A1 | 12/2005 | Colby et al. |
| 2005/0277998 A1 | 12/2005 | Tracey et al. |
| 2005/0283200 A1 | 12/2005 | Rezai et al. |
| 2005/0283201 A1 | 12/2005 | Machado et al. |
| 2005/0283208 A1 | 12/2005 | Von Arx et al. |
| 2005/0288600 A1 | 12/2005 | Zhang et al. |
| 2005/0288736 A1 | 12/2005 | Persen et al. |
| 2005/0288760 A1 | 12/2005 | Machado et al. |
| 2006/0009815 A1 | 1/2006 | Boveja |
| 2006/0020292 A1 | 1/2006 | Goetz et al. |
| 2006/0020491 A1 | 1/2006 | Mongeon et al. |
| 2006/0041222 A1 | 2/2006 | Dewing et al. |
| 2006/0041223 A1 | 2/2006 | Dewing et al. |
| 2006/0041287 A1 | 2/2006 | Dewing et al. |
| 2006/0047205 A1 | 3/2006 | Ludomirsky et al. |
| 2006/0052843 A1 | 3/2006 | Elsner et al. |
| 2006/0058597 A1 | 3/2006 | Machado et al. |
| 2006/0064133 A1 | 3/2006 | Von Arx et al. |
| 2006/0064134 A1 | 3/2006 | Mazar et al. |
| 2006/0064143 A1 | 3/2006 | Von Arx et al. |
| 2006/0069322 A1 | 3/2006 | Zhang et al. |
| 2006/0074450 A1 | 4/2006 | Boveja |
| 2006/0079936 A1 | 4/2006 | Boveja |
| 2006/0079942 A1 | 4/2006 | Deno et al. |
| 2006/0079945 A1 | 4/2006 | Libbus |
| 2006/0085046 A1 | 4/2006 | Rezai et al. |
| 2006/0094971 A1 | 5/2006 | Drew |
| 2006/0095081 A1 | 5/2006 | Zhou et al. |
| 2006/0100667 A1 | 5/2006 | Machado et al. |
| 2006/0106430 A1 | 5/2006 | Fowler et al. |
| 2006/0106431 A1 | 5/2006 | Wyler et al. |
| 2006/0111644 A1 | 5/2006 | Guttag et al. |
| 2006/0122525 A1 | 6/2006 | Shusterman |
| 2006/0122667 A1 | 6/2006 | Chavan et al. |
| 2006/0122864 A1 | 6/2006 | Gottesman et al. |
| 2006/0135877 A1 | 6/2006 | Giftakis et al. |
| 2006/0135881 A1 | 6/2006 | Giftakis et al. |
| 2006/0155495 A1 | 7/2006 | Osorio et al. |
| 2006/0161459 A9 | 7/2006 | Rosenfeld et al. |
| 2006/0167497 A1 | 7/2006 | Armstrong et al. |
| 2006/0173493 A1 | 8/2006 | Armstrong et al. |
| 2006/0173522 A1 | 8/2006 | Osorio |
| 2006/0190056 A1 | 8/2006 | Fowler et al. |
| 2006/0195155 A1 | 8/2006 | Firlik et al. |
| 2006/0195163 A1 | 8/2006 | KenKnight et al. |
| 2006/0200206 A1 | 9/2006 | Firlik et al. |
| 2006/0212091 A1 | 9/2006 | Lozano et al. |
| 2006/0217780 A1 | 9/2006 | Gliner et al. |
| 2006/0220839 A1 | 10/2006 | Fifolt et al. |
| 2006/0224067 A1 | 10/2006 | Giftakis et al. |
| 2006/0224191 A1 | 10/2006 | DiLorenzo |
| 2006/0241697 A1 | 10/2006 | Libbus et al. |
| 2006/0241725 A1 | 10/2006 | Libbus et al. |
| 2006/0247698 A1* | 11/2006 | Burnes et al. .................. 607/9 |
| 2006/0253164 A1 | 11/2006 | Zhang et al. |
| 2006/0253168 A1 | 11/2006 | Wyler et al. |
| 2006/0253169 A1 | 11/2006 | Wyler et al. |
| 2006/0253170 A1 | 11/2006 | Wyler et al. |
| 2006/0253171 A1 | 11/2006 | Wyler et al. |
| 2006/0259095 A1 | 11/2006 | Wyler et al. |
| 2006/0264730 A1 | 11/2006 | Stivoric et al. |
| 2006/0265018 A1 | 11/2006 | Smith et al. |
| 2006/0271409 A1 | 11/2006 | Rosenfeld et al. |
| 2006/0293720 A1 | 12/2006 | DiLorenzo |
| 2007/0027486 A1 | 2/2007 | Armstrong et al. |
| 2007/0032734 A1 | 2/2007 | Najafi et al. |
| 2007/0032834 A1 | 2/2007 | Gliner et al. |
| 2007/0038262 A1 | 2/2007 | Kieval et al. |
| 2007/0043392 A1 | 2/2007 | Gliner et al. |
| 2007/0055320 A1 | 3/2007 | Weinand et al. |
| 2007/0073150 A1 | 3/2007 | Gopalsami et al. |
| 2007/0073346 A1 | 3/2007 | Corbucci et al. |
| 2007/0073355 A1 | 3/2007 | DiLorenzo |
| 2007/0078491 A1 | 4/2007 | Siejko et al. |
| 2007/0088403 A1 | 4/2007 | Wyler et al. |
| 2007/0088404 A1 | 4/2007 | Wyler et al. |
| 2007/0088405 A1 | 4/2007 | Jacobson et al. |
| 2007/0100278 A1 | 5/2007 | Frei et al. |
| 2007/0100397 A1 | 5/2007 | Seeberger et al. |
| 2007/0100398 A1 | 5/2007 | Sloan |
| 2007/0112393 A1 | 5/2007 | Gliner et al. |
| 2007/0123946 A1 | 5/2007 | Masoud |
| 2007/0135855 A1 | 6/2007 | Foshee et al. |
| 2007/0142862 A1 | 6/2007 | DiLorenzo |
| 2007/0142873 A1 | 6/2007 | Esteller et al. |
| 2007/0149952 A1 | 6/2007 | Bland et al. |
| 2007/0150011 A1 | 6/2007 | Meyer et al. |
| 2007/0150014 A1 | 6/2007 | Kramer et al. |
| 2007/0150024 A1 | 6/2007 | Leyde et al. |
| 2007/0150025 A1 | 6/2007 | DiLorenzo et al. |

| | | |
|---|---|---|
| 2007/0156179 A1 | 7/2007 | Karashurov |
| 2007/0156450 A1 | 7/2007 | Roehm et al. |
| 2007/0156626 A1 | 7/2007 | Roehm et al. |
| 2007/0161919 A1 | 7/2007 | DiLorenzo |
| 2007/0162086 A1 | 7/2007 | DiLorenzo |
| 2007/0167991 A1 | 7/2007 | DiLorenzo |
| 2007/0173901 A1 | 7/2007 | Reeve |
| 2007/0179534 A1 | 8/2007 | Firlik et al. |
| 2007/0179558 A1 | 8/2007 | Gliner et al. |
| 2007/0179584 A1 | 8/2007 | Gliner |
| 2007/0203548 A1 | 8/2007 | Pawelzik et al. |
| 2007/0208212 A1 | 9/2007 | DiLorenzo |
| 2007/0208390 A1 | 9/2007 | Von Arx et al. |
| 2007/0213785 A1 | 9/2007 | Osorio et al. |
| 2007/0233192 A1 | 10/2007 | Craig |
| 2007/0238939 A1 | 10/2007 | Giftakis et al. |
| 2007/0239210 A1 | 10/2007 | Libbus et al. |
| 2007/0239211 A1 | 10/2007 | Lorincz et al. |
| 2007/0239220 A1 | 10/2007 | Greenhut et al. |
| 2007/0244407 A1 | 10/2007 | Osorio |
| 2007/0249953 A1 | 10/2007 | Frei et al. |
| 2007/0249954 A1 | 10/2007 | Virag et al. |
| 2007/0250130 A1 | 10/2007 | Ball et al. |
| 2007/0250145 A1 | 10/2007 | Kraus et al. |
| 2007/0255147 A1 | 11/2007 | Drew et al. |
| 2007/0255155 A1 | 11/2007 | Drew et al. |
| 2007/0255330 A1 | 11/2007 | Lee et al. |
| 2007/0255337 A1 | 11/2007 | Lu |
| 2007/0260147 A1 | 11/2007 | Giftakis et al. |
| 2007/0260289 A1 | 11/2007 | Giftakis et al. |
| 2007/0265489 A1 | 11/2007 | Fowler et al. |
| 2007/0265508 A1 | 11/2007 | Sheikhzadeh-Nadjar et al. |
| 2007/0265536 A1 | 11/2007 | Giftakis et al. |
| 2007/0272260 A1 | 11/2007 | Nikitin et al. |
| 2007/0282177 A1 | 12/2007 | Pilz |
| 2007/0287931 A1 | 12/2007 | DiLorenzo |
| 2007/0288072 A1 | 12/2007 | Pascual-Leone et al. |
| 2007/0299349 A1 | 12/2007 | Alt et al. |
| 2007/0299473 A1 | 12/2007 | Matos |
| 2007/0299480 A1 | 12/2007 | Hill |
| 2008/0015651 A1 | 1/2008 | Ettori et al. |
| 2008/0015652 A1 | 1/2008 | Maile et al. |
| 2008/0021332 A1 | 1/2008 | Brainard, III |
| 2008/0021341 A1 | 1/2008 | Harris et al. |
| 2008/0021517 A1 | 1/2008 | Dietrich |
| 2008/0021520 A1 | 1/2008 | Dietrich |
| 2008/0027347 A1 | 1/2008 | Harris et al. |
| 2008/0027348 A1 | 1/2008 | Harris et al. |
| 2008/0027515 A1 | 1/2008 | Harris et al. |
| 2008/0033502 A1 | 2/2008 | Harris et al. |
| 2008/0033503 A1 | 2/2008 | Fowler et al. |
| 2008/0033508 A1 | 2/2008 | Frei et al. |
| 2008/0039895 A1 | 2/2008 | Fowler et al. |
| 2008/0046035 A1 | 2/2008 | Fowler et al. |
| 2008/0046037 A1 | 2/2008 | Haubrich et al. |
| 2008/0046038 A1 | 2/2008 | Hill et al. |
| 2008/0051852 A1 | 2/2008 | Dietrich et al. |
| 2008/0058884 A1 | 3/2008 | Matos |
| 2008/0064934 A1 | 3/2008 | Frei et al. |
| 2008/0071323 A1 | 3/2008 | Lowry et al. |
| 2008/0077028 A1 | 3/2008 | Schaldach et al. |
| 2008/0081962 A1 | 4/2008 | Miller et al. |
| 2008/0082132 A1 | 4/2008 | Annest et al. |
| 2008/0103548 A1 | 5/2008 | Fowler et al. |
| 2008/0114417 A1 | 5/2008 | Leyde |
| 2008/0119900 A1 | 5/2008 | DiLorenzo |
| 2008/0125820 A1 | 5/2008 | Stahmann et al. |
| 2008/0139870 A1 | 6/2008 | Gliner et al. |
| 2008/0146890 A1 | 6/2008 | LeBoeuf et al. |
| 2008/0146959 A1 | 6/2008 | Sheffield et al. |
| 2008/0161712 A1 | 7/2008 | Leyde |
| 2008/0161713 A1 | 7/2008 | Leyde et al. |
| 2008/0161879 A1 | 7/2008 | Firlik et al. |
| 2008/0161880 A1 | 7/2008 | Firlik et al. |
| 2008/0161881 A1 | 7/2008 | Firlik et al. |
| 2008/0161882 A1 | 7/2008 | Firlik et al. |
| 2008/0183096 A1 | 7/2008 | Snyder et al. |
| 2008/0183097 A1 | 7/2008 | Leyde et al. |
| 2008/0183245 A1 | 7/2008 | Van Oort et al. |
| 2008/0195175 A1 | 8/2008 | Balzer et al. |
| 2008/0200925 A1 | 8/2008 | Johnson et al. |
| 2008/0208013 A1 | 8/2008 | Zhang et al. |
| 2008/0208074 A1 | 8/2008 | Snyder et al. |
| 2008/0208285 A1 | 8/2008 | Fowler et al. |
| 2008/0208291 A1 | 8/2008 | Leyde et al. |
| 2008/0208781 A1 | 8/2008 | Snyder |
| 2008/0215112 A1 | 9/2008 | Firlik et al. |
| 2008/0215114 A1 | 9/2008 | Stuerzinger et al. |
| 2008/0221644 A1 | 9/2008 | Vallapureddy et al. |
| 2008/0234598 A1 | 9/2008 | Snyder et al. |
| 2008/0249591 A1 | 10/2008 | Gaw et al. |
| 2008/0255582 A1 | 10/2008 | Harris |
| 2009/0054795 A1 | 2/2009 | Misczynski et al. |
| 2009/0076567 A1 | 3/2009 | Fowler et al. |
| 2009/0318779 A1* | 12/2009 | Tran .................. 600/301 |

FOREIGN PATENT DOCUMENTS

| | | |
|---|---|---|
| EP | 0402683 | 12/1990 |
| EP | 0713714 | 5/1996 |
| EP | 1139861 | 12/1999 |
| EP | 1070518 | 1/2001 |
| EP | 0944411 | 4/2001 |
| EP | 1145736 A2 | 10/2001 |
| EP | 1483020 | 12/2004 |
| EP | 1486232 | 12/2004 |
| EP | 1595497 | 11/2005 |
| EP | 1120130 | 12/2005 |
| EP | 1647300 | 4/2006 |
| EP | 1202775 | 9/2006 |
| GB | 2026870 | 2/1980 |
| GB | 2079610 | 1/1982 |
| WO | 9302744 | 2/1993 |
| WO | 9417771 | 8/1994 |
| WO | 0064336 A1 | 11/2000 |
| WO | 0108749 | 2/2001 |
| WO | 0064336 A9 | 6/2002 |
| WO | 03085546 | 10/2003 |
| WO | 2004036377 | 4/2004 |
| WO | 2004064918 | 8/2004 |
| WO | 2004069330 | 8/2004 |
| WO | 2004071575 | 8/2004 |
| WO | 2004075982 | 9/2004 |
| WO | 2004112894 | 12/2004 |
| WO | 2005007120 | 1/2005 |
| WO | 2005007232 | 1/2005 |
| WO | 2005028026 A1 | 3/2005 |
| WO | 2005053788 | 6/2005 |
| WO | 2005067599 | 7/2005 |
| WO | 2005101282 | 10/2005 |
| WO | 2006014760 | 2/2006 |
| WO | 2006019822 | 2/2006 |
| WO | 2006050144 | 5/2006 |
| WO | 2006122148 | 11/2006 |
| WO | 2007066343 A2 | 6/2007 |
| WO | 2007072425 | 6/2007 |
| WO | 2007124126 | 11/2007 |
| WO | 2007124190 | 11/2007 |
| WO | 2007124192 | 11/2007 |
| WO | 2007142523 | 12/2007 |

OTHER PUBLICATIONS

Bohning, D.E., et al.; "Feasibility of Vagus Nerve Stimulation—Synchronized Blood Oxygenation Level-Dependent Functional MRI," A Journal of Clinical and Laboratory Research: Investigative Radiology; vol. 36, No. 8 (Aug. 2001); pp. 470-479.

Boon, Paul, et al.; "Programmed and Magnet-Induced Vagus Nerve Stimulation for Refractory Epilepsy;" Journal of Clinical Neurophysiology vol. 18 No. 5; (2001); pp. 402-407.

Clark, K.B., et al.; "Posttraining Electrical Stimulation of Vagus Afferents with Concomitant Vagal Efferent Inactivation Enhances Memory Storage Processes in the Rat," Neurobiology of Learning and Memory, vol. 70, 364-373 (1998) Art. No. NL983863.

Clark, K.B., et al.; "Enhanced Recognition Memory Following Vagus Nerve Stimulation in Human Subjects;" Nature Neuroscience, vol. 2, No. 1, (Jan. 1999) pp. 93-98.

Craig, A.D. (Bud); "Distribution of Trigeminothalamic and Spinothalamic Lamina I Terminations in the Macaque Monkey;" The Journal of Comparative Neurology, vol. 477, pp. 119-148 (2004).

DeGiorgo, Christopher M., et al.; "Vagus Nerve Stimulation; Analysis of Device Paramters in 154 Patients During the Long-Term XE5 Study;" Epilepsia, vol. 42, No. 8; pp. 1017-1020 (2001).

Devous, Michael D., et al.; "Effects of Vagus Nerve Stimulation on Regional Cerebral Blood Flow in Treatment-Resistant Depression," National Institute of Mental Health—42nd Annual NCDEU Meeting: Poster Session II; Poster Abstracts, Jun. 10-13, 2002, 1 page; http://www.nimh.nih.gov/ncdeu/abstracts2002/ncdeu2019.cfm.

Hallowitz, R.A., et al.; "Effects of Vagal Tolleys on Units of Intralaminar and Juxtalaminar Thalamic Nuclei in Monkeys;"Brain Research, vol. 130 (1977), pp. 271-286.

Harry, J.D., et al.; "Balancing Act: Noise is the Key to Restoring the Body's Sense of Equilibrium;" IEEE Spectrum (Apr. 2005)pp. 37-41.

Henry, T.R., et al.; "Brain Blood-Flow Alterations Induced by Therapeutic Vagus Nerve Stimulation in Partial Epilepsy: I. Acute Effects at High and Low Levels of Stimulation;" Epilepsia vol. 39, No. 9; pp. 984-990 (1998).

Henry, MD, T.R.; "Therapeutic Mechanisms of Vagus Nerve Stimulation" Neurology, vol. 59 Suppl. 4 (Sep. 2002); pp. S3-S14.

King, M.D., "Effects of Short-Term Vagus Nerve Stimulation (VNS) on FOS Expression in Rat Brain Nuclei" 58th Annual Scientific Convention of the Society of Biological Psychaitry, (May 2003).

Klapper, M.D., et al., "VNS Therapy Shows Potential Benefit in Patients with Migraine and Chronic Daily Headache After 3 to 6 Months of Treatment (Preliminary Results)" 45th Annual Scientific Meeting of the American Headache Society (Jun. 2003).

Koo, B., "EEG Changes With Vagus Nerve Stimulation" Journal of Clinical Neurophysiology, vol. 18 No. 5 (Sep. 2001); pp. 434-441.

Labar, D., "Vagus Nerve Stimulation for 1 Year in 269 patients on Unchanged Antiepilectic Drugs" Seizure vol. 13, (2004) pp. 392-398.

Lockard et al., "Feasibility and Safety of Vagal Stimulation in Monkey Model;" Epilepsia, vol. 31 (Supp. 2) (1990), pp. S20-S26.

Liebman, K.M. et al.; "Improvement in Cognitive Function After Vagal Nerve Stimulator Implantation;" Epilepsia, vol. 39, Suppl. 6 (1998) 1 page.

Malow, B.A., et al.; "Vagus Nerve Stimulation Reduces Daytime Sleepiness in Epilepsy Patients" Neurology 57 (2001) pp. 879-884.

McClintock, P., "Can Noise Actually Boost Brain Power" Physics World Jul. 2002; pp. 20-21.

Mori, T., et al.; "Noise-Induced Entrainment and Stochastic Resonance in Human Brain Waves" Physical Review Letters vol. 88, No. 21 (2002); pp. 218101-1-218101-4.

Rugg-Gunn, F.J., et al.; "Cardiac Arrhythmias in Focal Epilepsy; a Prospective Long-Term Study" www.thelancet.com vol. 364 (2004) pp. 2212-2219.

Rutecki, P.; "Anatomical, Physiological, and Theoretical Basis for the Antiepileptic Effect of Vagus Nerve Stimulation" Epilepsia, vol. 31 Suppl. 2; S1-S6 (1990).

Sahin, M.; et al.; "Improved Nerve Cuff Electrode Recordings with Subthreshold Anodic Currents;" IEEE Transactions on Biomedical Engineering, vol. 45, No. 8 (Aug. 1998) pp. 1044-1050.

Schachter, S.C., et al.; "Progress in Epilepsy Research: Vagus Nerve Stimulation;" Epilepsia, vol. 39, No. 7 (1998) pp. 677-686.

Tatum, W.O., et al.; "Ventricular Asystole During Vagus Nerve Stimulation and Epilepsy in Humans" American Academy of Neurologgy (1999) p. 1267 (see also pp. 1117, 1166, and 1265).

Tatum, W.O., et al.; "Vagus Nerve Stimulation and Drug Reduction" Neurology, vol. 56 No. 4 (Feb. 2001) pp. 561-563.

Terry et al.; "The Implantable Neyrocybernetic Prosthesis System", Pacing and Clinical Electrophysiology, vol. 14, No. 1 (Jan. 1991), pp. 86-93.

Tubbs, R.S., et al.; "Left-Sided Vagus Nerve Stimulation Decreases Intracranial Pressure Without Resultant Bradycardia in the Pig: A Potential Therapeutic Modality for Humans" Child's Nervous System Original Paper; Springer-Verlag 2004.

Valdez-Cruz, A., et al.; "Chronic Stimulation of the Cat Vagus Nerve Effect on Sleep and Behavior" Progress in Neuro-Psychopharmacology & Biological Psychiatry, vol. 26 (2002) pp. 113-118.

Vonck, K., et al. "The Mechanism of Action of Vagus Nerve Stimulation for Refractory Epilepsy—The Current Status", Journal of Neurophysiology, vol. 18 No. 5 (2001), pp. 394-401.

Ward, H., M.D., et al.; "Treatment-Refractory Obsessive-Compulsive Disorder: Potential Benefit of VNS Therapy" 23rd Annual Conference of the Anxiety Disorders Association of America (2007).

Woodbury, et al., "Vagal Stimulation Reduces the Severity of Maximal Electroshock Seizures in Intact Rats. Use of a Cuff Electrode for Stimulating and Recording"; Pacing and Clinical Electrophysiology, vol. 14 (Jan. 1991), pp. 94-107.

Zabara, J. "Inhibition of Experimental Seizures in Canines by Repetivie Vagal Stimulation" Epilepsia vol. 33, No. 6 (1992); pp. 1005-1012.

Dodrill, Ph.D., et al.; "Effects of Vagal Nerve Stimulation on Cognition and Quality of Life in Epilepsy;" Epilepsy and Behavior, vol. 2 (2001); pp. 46-53.

Fromes, G. A.et al.; "Clinical Utility of On-Demand Magnet use with Vagus Nerve Stimulation;" AES Proceedings, p. 117.

George, M.S., et al.; "Open Trial of VNS Therapy in Severe Anxiety Disorders;" 156th American Psychiatric Association Annual Meeting; May 17-22, 2003.

George, M.S., et al.; "Vagus Nerve Stimulation: A New Tool for Brain Research and Therapy;" Society of Biological Psychaitry vol. 47 (2000) pp. 287-295.

Fanselow, E.E., at al.; "Reduction of Pentylenetetrazole-Induced Seizure Activity in Awake Rates by Seizure-Triggered Trigeminal Nerve Stimulation;" The Journal of Neuroscience, Nov. 1, 2000; vol. 20/21 ; pp. 8160-8168.

* cited by examiner

IMPLANTABLE NEUROSTIMULATOR WITH REFRACTORY STIMULATION

BACKGROUND

Implantable neurostimulators are effective at treating various disorders such as epilepsy and depression. A neurostimulator is implanted in the patient and connected via one or more electrodes to a target nerve, such as the vagus nerve. Current from the electrical signal provided by the neurostimulator or action potentials evoked by the stimulated target nerve can propagate to a non-target nerve (including nerves nearby the target nerve as well as specific non-target fibers within the target nerve) and non-target muscle tissue adjacent to the electrodes. As a result, such nearby tissues may be stimulated thereby resulting in wasted energy that is non-therapeutic and which may in addition cause undesired side effects such as contractions of the muscle tissue. For example, it is possible for vagus nerve stimulation to excite the muscles at or near the patient's vocal cords thereby potentially causing hoarseness. While generally regarded as benign, the excitation of muscle tissue and the resultant hoarseness may be uncomfortable to the patient and is at any rate undesired, wasteful and non-therapeutic. Ameliorating the foregoing problems while improving the efficacy of the underlying therapy provided by the neurostimulator is desirable.

BRIEF SUMMARY

In accordance with at least one embodiment of the invention, an implantable medical device comprises a neurostimulator that provides a first electrical signal to a nerve (e.g., the vagus nerve) in a first, non-refractory period. The first electrical signal is adapted to induce action potentials in one or more target axons (fibers) of the nerve. The neurostimulator also provides a second electrical signal to the nerve during a second period in which one or more of the non-target tissues (e.g. adjacent muscles or non-target nerve fibers) are refractory. The second period may comprise at least a portion of one or both of an absolute refractory period and a relative refractory period for the non-target tissue. The second signal provided to the nerve during the refractory period causes the refractory period of the non-target tissue to be altered, i.e., extended or shortened, depending on the attributes of the second signal. Extending the refractory period ameliorates various side effects that might otherwise occur. Shortening the relative refractory period facilitates additional therapies to be implemented.

In accordance with some embodiments, a method comprises applying a first electrical signal to a nerve to evoke an action potential. As a result, the nerve enters a refractory period in which the nerve is refractory to further induction of action potentials. During the refractory period, the method also comprises providing a second electrical signal to the nerve thereby altering the refractory period.

In accordance with another embodiment, a method comprises applying a first electrical signal to a nerve to evoke an action potential. The first electrical signal or action potential evokes action potentials in non-target tissue. The non-target tissue thereafter enters a refractory period in which the non-target tissue is refractory to further induction of action potentials. During the refractory period, the method further comprises applying a second electrical signal to the nerve thereby altering the refractory period of the non-target tissue.

In accordance with another embodiment, an implantable neurostimulator comprises an electrical signal generator and an electrode coupled to the electrical signal generator. The electrode is adapted to couple to a nerve. The electrical signal generator applies a first electrical signal to a nerve to evoke an action potential. As a result, the nerve enters a refractory period in which the nerve is in a refractory state. During the refractory period, the electrical signal generator provides a second electrical signal to the nerve thereby altering the refractory period of the nerve.

In accordance with yet another embodiment, an implantable neurostimulator comprises an electrical signal generator and an electrode. The electrode is adapted to be coupled to the electrical signal generator and to a nerve to thereby provide therapy to a target nerve fiber. The electrical signal generator applies a first electrical signal to a nerve to evoke an action potential in the target nerve which causes an action potential to be evoked in a non-target nerve fiber or tissue. The non-target nerve fiber or tissue thereby enters a refractory period in which the non-target nerve fiber or tissue is in a refractory state. During the refractory period, the electrical signal generator applies a second electrical signal to the nerve fiber or tissue thereby altering the refractory period of the non-target nerve fiber or tissue.

BRIEF DESCRIPTION OF THE DRAWINGS

For a detailed description of exemplary embodiments of the invention, reference will now be made to the accompanying drawings in which.

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and is not intended to limit the scope of the disclosure, including the claims, to that embodiment.

Figure 1:
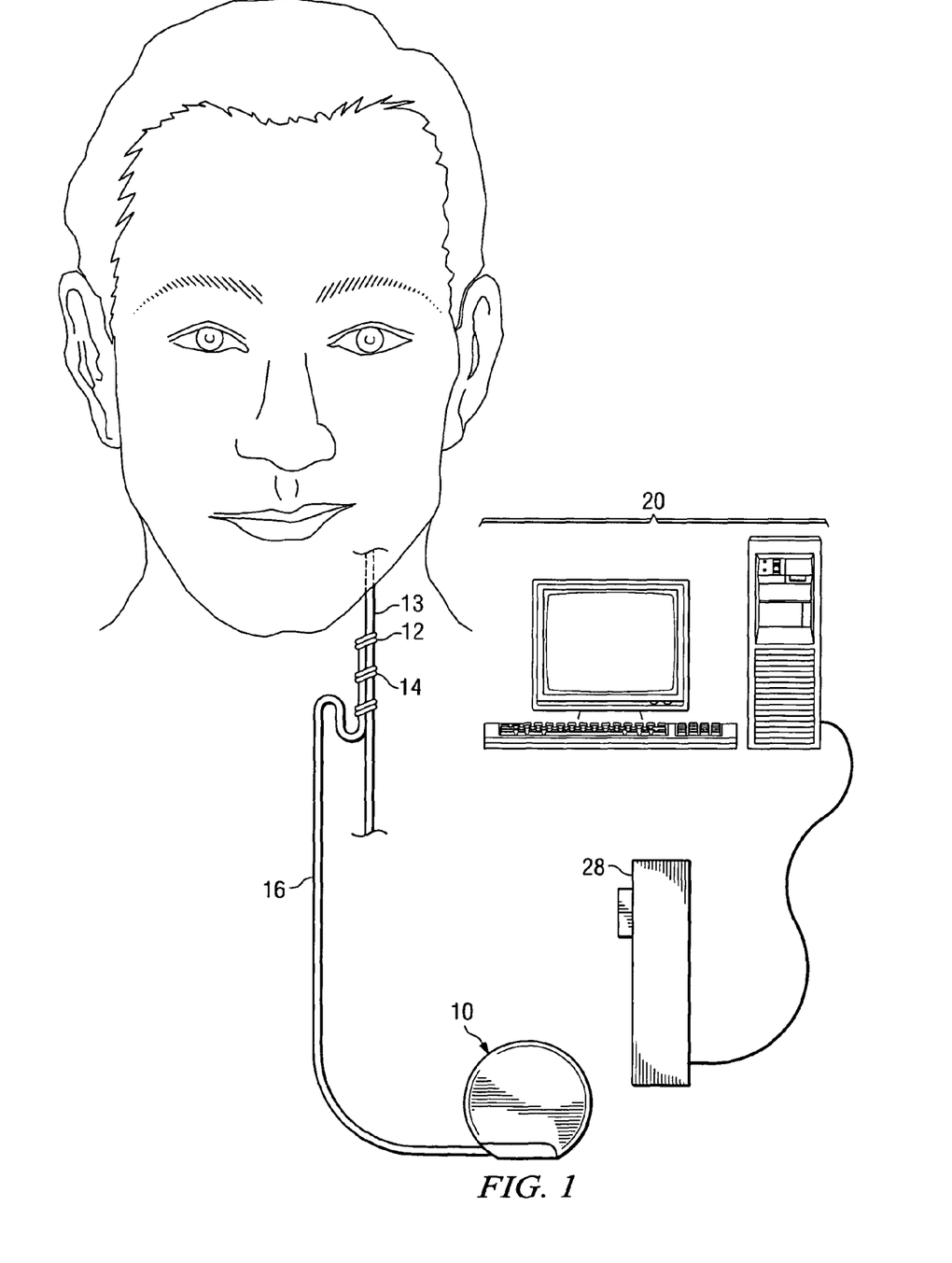
FIG. 1 depicts, in schematic form, an implantable neurostimulator, in accordance with a preferred embodiment of the invention, implanted within a patient and programmable by an external programming system.

FIG. 1 illustrates an implantable medical device ("IMD") 10 implanted in a patient. The IMD 10 may be representative of any of a variety of medical devices. At least one preferred embodiment of the IMD 10 comprises a neurostimulator for stimulating a neural structure in a patient, particularly a neurostimulator for stimulating a patient's cranial nerve such as a vagus nerve 13. Although the IMD 10 is described below in terms of a vagus nerve stimulation ("VNS") embodiment, the disclosure and claims that follow are not limited to VNS unless expressly noted, and may be applied to the stimulation of other tissues such as the trigeminal and/or glossopharyngeal nerves, or to other neural tissue such as one or more brain structures of the patient, spinal nerves, and other spinal structures, as well as various non-neural tissues and organs.

Referring still to FIG. 1, a lead assembly 16 comprising one or more leads is coupled to the IMD 10. The lead assembly 16 includes one or more electrodes, such as electrodes 12 and 14. Each lead assembly 16 has a proximal end that connects to the IMD 10. The electrodes 12, 14 are coupled to a distal end of the lead assembly. At least one electrode 12 or 14, and preferably an electrode pair (12 and 14), is used as a therapeutic electrode to deliver an electrical signal to target tissues such as the patient's vagus nerve 13. At least one electrode 12, 14 (preferably an electrode pair 12 and 14) may in some embodiments be used as a sensing electrode to detect electrical activity of target tissue (e.g., the vagus nerve 13). In alternative embodiments, separate sensing electrode(s) may be used. The housing (or "can") of the IMD 10 may also be used as a stimulating or sensing electrode. Sensing electrodes may alternatively be omitted entirely.

FIG. 1 also illustrates an external device implemented as a programming system 20 for the IMD 10. The programming system 20 may comprise a personal computer, a handheld computer such as a personal digital assistant (PDA) device, or other suitable computing device consistent with the description contained herein, as well as a wand 28 used for transmitting and receiving signals to and from the IMD 10. In systems where the programming system 20 uses one or more channels in the Medical Implant Communications Service (MICS) bandwidths, the wand 28 may be omitted to permit more convenient communication between the programming system and the IMD 10. Methods and apparatus for communication between the IMD 10 and an external programming system 20 are known in the art, including telemetry via an RF communication link. Representative techniques for such communication are disclosed in U.S. Pat. No. 5,304,206, and U.S. Pat. No. 5,235,980, both incorporated herein by reference. The IMD 10 includes a transceiver (such as a coil) that permits signals to be communicated wirelessly between the programming system 20 and/or wand 28 and the IMD 10. The programming system 20 monitors the performance of the IMD 10 and downloads new executable operational programming (i.e., software) and/or therapy parameters into the IMD 10 to alter its operation as desired. In accordance with preferred embodiments of the invention and as further explained below, the programming system 20 downloads configuration parameters that cause the IMD 10 to extend or shorten the refractory period of either the nerve 13 being stimulated or non-target tissue in or near the nerve.

Figure 2:
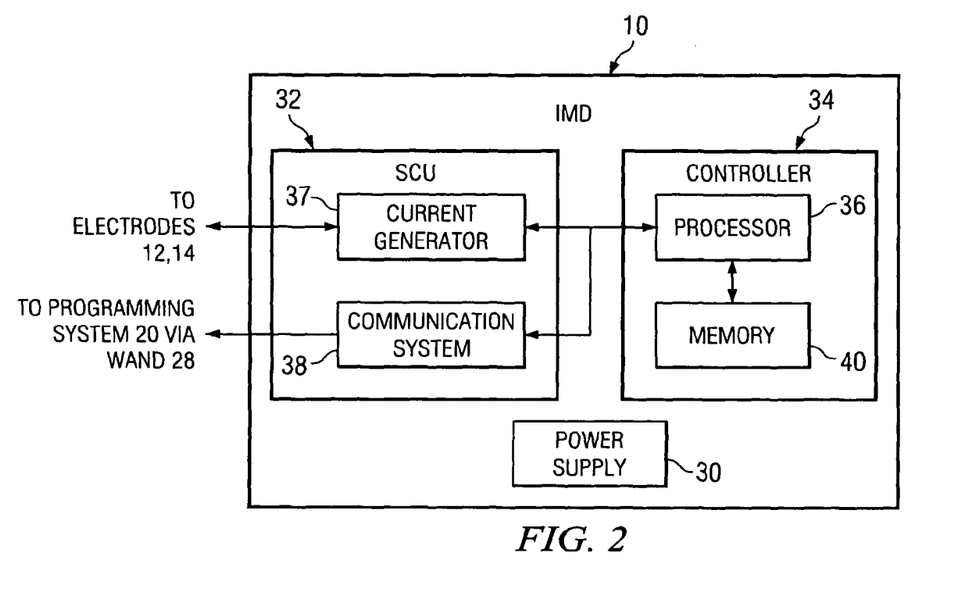
FIG. 2 shows an illustrative embodiment of the implantable neurostimulator of FIG. 1.

FIG. 2 shows a block diagram of a preferred embodiment of the IMD 10. As shown, the IMD 10 includes a power supply 30 (e.g., a battery), a stimulation and communication unit ("SCU") 32, and a controller 34. The illustrative SCU 32 of FIG. 2 comprises a current generator 37 and a communication system 38. Under the control of controller 34, the current generator 37 of the SCU 32 generates an electrical signal (e.g., a programmable, constant current pulsed signal) to stimulate a target neural tissue in a patient. Further, under the control of controller 34, the communication system 38 of the SCU 32 telemeters data (e.g., therapy parameters) or operational programming (e.g., executable software) to/from the programming system 20. In the embodiment of FIG. 2, the battery 30 provides power for both the SCU 32 and the controller 34.

The controller 34 generally assists, controls, and/or programs the SCU 32. Controller 34 preferably comprises a processor 36 such as a low-power, mixed-signal microcontroller. One suitable processor is available from Texas Instruments, Inc., selected from the MSP430F family of processors. Other suitable processors from the PIC1xF family of processors are available from MicroChip Technology. Other suitable processors may be used and/or integrated into the controller 34, although the processor 36 preferably is capable of processing a variety of sensor inputs, uses low power, and operates at a high speed. In general, however, any suitable processor 36 can be used in the controller 34 to implement the functionality performed by the controller 34 as explained herein. It will be appreciated that some features of the controller 34 may also be provided in whole or in part by the SCU 32, and vice versa. Thus, while certain features of preferred embodiments of the present invention may be described as comprising part of the SCU 32, it is not intended thereby to preclude embodiments in which the features are provided by the controller 34. Likewise, certain features described herein as comprising part of the controller 34 are not intended to preclude embodiments in which the features comprise part of the SCU 32.

In the embodiment of FIG. 2, the controller 34 additionally comprises a memory 40 integrated into the controller. In some embodiments, the processor 36 of the controller 34 directly executes programs from the integrated memory 40. That is, executable instructions (i.e., operational programming) can be fetched directly from memory 40 for execution by the processor 36 without first copying the instructions to another memory (e.g., a RAM). The integrated memory 40 may be upgraded by erasing one or more segments of the integrated memory 40 and, via the programmer 20, writing a new program to the integrated memory 40.

The external programming system 20 can wirelessly transmit programs and configuration data to the IMD 10 for storage in the IMD's memory 40, registers internal to the processor 36, or other storage of the IMD 10.

Like all electrically-excitable tissue, neural tissue, such as the vagus nerve, has an intrinsic property called the "refractory period." Once a nerve is excited (i.e., an action potential is generated), the nerve enters the refractory period during which time the nerve is resistant to further induction of action potentials, even if another or additional electrical current is applied to the nerve. During this time period, the nerve is said to be "refractory" to an applied electrical signal. In general, action potentials can again be induced in the nerve with an applied electrical signal once the refractory period is over.

Figure 3:
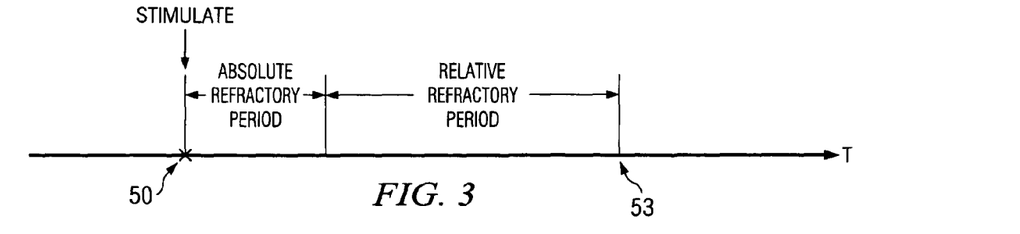
FIG. 3 illustrates a refractory period of an electrically-excitable tissue as comprising an absolute refractory period and a relative refractory period.

As illustrated by FIG. 3, the refractory period comprises an "absolute" refractory period followed by a "relative" refractory period. The absolute refractory period begins upon the stimulation of a nerve at 50. During the absolute refractory period, the nerve cannot be induced to generate an action potential regardless of the strength of the applied electrical signal. During the relative refractory period, which immediately follows the absolute refractory period, it is possible to induce an action potential in the nerve with a sufficiently strong applied electrical signal. A stronger electrical signal is required to generate an action potential during the relative refractory period than to initially stimulate the nerve during a non-refractory period. The lengths of the absolute and relative refractory periods may be altered by applying an electrical signal to the nerve during one or both of the absolute and relative refractory periods. The duration of the absolute and relative refractory periods without an externally applied signal are relatively constant for a particular tissue, and are referred to herein as the "intrinsic" absolute and relative refractory periods. The nerve's intrinsic relative refractory period ends at reference numeral 53 in FIG. 3.

Muscle tissue (e.g., the heart) is also characterized by a refractory period. Different types of muscular and neural tissues have different refractory periods. The refractory period of cardiac tissue tends to be substantially longer than the refractory period of neural tissue. Further, the vagus nerve comprises different types of nerve fibers, e.g., A fibers, B fibers and C fibers, with many subtypes. A and B vagus nerve fibers have larger diameters than C fibers. C fibers tend to have substantially longer refractory periods than A and B fibers, and B fibers have slightly longer refractory periods than A fibers.

Without limiting the scope of this disclosure, Table I below provides exemplary values for the absolute and relative refractory periods of various types of nerves and tissues. In general muscle tissues have substantially longer refractory periods than nerve tissues.

TABLE I

| Tissue type | Absolute Refractory (mS) | Relative Refractory (mS) |
| --- | --- | --- |
| Large diameter nerve (e.g., A and B fiber types) | 0.4 | Up to 1.6 |
| Small diameter nerve (e.g., C fiber type) | 4 | Up to 16 |
| Cardiac muscle | 100 | Up to 400 |

In accordance with various embodiments of the invention, the IMD 10 alters the length of the refractory period and, in some embodiments, specifically the relative refractory period. In some embodiments, the IMD 10 extends the relative refractory period, while in other embodiments, the IMD 10 shortens the relative refractory period. Further still, in some embodiments, the IMD 10 extends the relative refractory period in accordance with some therapies or situations, while shortening the relative refractory in accordance with other therapies or situations. Extending a relative refractory period can be accomplished by providing an electrical signal to the nerve during the relative refractory period at a level low enough so as not to re-stimulate the nerve. Shortening the relative refractory period can be accomplished by providing a signal during the relative refractory period with a polarity opposite to that of the first electrical signal that induced the action potential.

Figure 4:
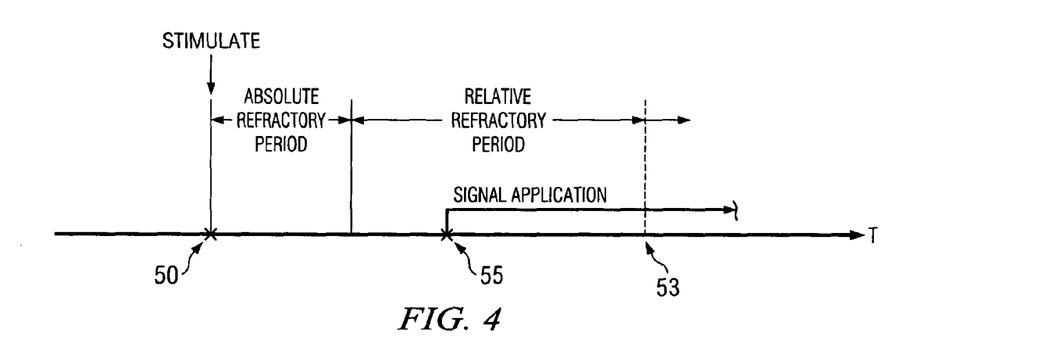
FIG. 4 illustrates an embodiment in which the relative refractory period is extended by providing an electrical signal during the relative refractory period.

FIG. 4 depicts a timeline in which a second electrical signal 55 to alter the refractory period of the nerve is applied to the nerve beginning at a time in the relative refractory period of the nerve. The end of the nerve's intrinsic relative refractory period (53) is extended due to the application of the signal at 55. The relative refractory period can be extended almost indefinitely as long as the signal continues to be or is repetitively applied. However, the tissue will eventually either exit a refractory state or become permanently damaged or impaired, even with an applied current. Once the application of the signal is removed, the relative refractory period of the nerve will subsequently end, after which the nerve returns to a non-refractory state in which action potentials can again be induced with a first electrical signal.

Extending the relative refractory is useful to ameliorate side effects that might otherwise be caused by the IMD 10. For example, action potentials generated by applying a first electrical signal to a vagus nerve of a patient may propagate to adjacent muscle tissues. Such muscle tissues may include muscles adjacent to, or that directly control, the patient's vocal cords. As a result of stimulating the patient's vagus nerve, the patient's vocal cords, or controlling muscles, may be affected possibly resulting in hoarseness or changes to the patient's voice during delivery of a first electrical signal. All tissues stimulated by the first electrical signal, including both target nerve fibers and non-target nerve fibers or muscles, will begin their respective intrinsic refractory periods approximately synchronous with the first electrical signal. However, the difference between intrinsic refractory periods of different tissues may be exploited to ameliorate undesired side effects.

In accordance with at least some embodiments, the current generator 37 of the IMD 10 provides a second electrical signal during the relative refractory period of at least one non-target tissue, such as a particular nerve fiber type, or muscle tissue. The magnitude of the second electrical signal is small enough to prevent additional action potentials from being generated. Instead, the second electrical signal provided to the nerve causes the non-target tissue, which is in a refractory state, to remain in a refractory state, thereby extending the duration of the relative refractory period. By extending the relative refractory period of the non-target tissue, no additional action potentials will be induced that otherwise would propagate to, and stimulate, adjacent tissues. In at least some such embodiments, the relative refractory period is extended as long as the second electrical signal continues to be applied to the nerve.

The magnitude of the second electrical signal used to extend the relative refractory period depends, at least in part, on the point in time during the relative refractory period at which the second electrical signal is first applied to the nerve. The earlier in the relative refractory period that the second electrical signal is applied, the larger the magnitude the second electrical signal needs to be to cause the relative refractory period to be extended. By contrast, the later in the relative refractory period that the current is applied, the smaller the magnitude of the current needs to be to cause the relative refractory period to be extended.

Figure 5:
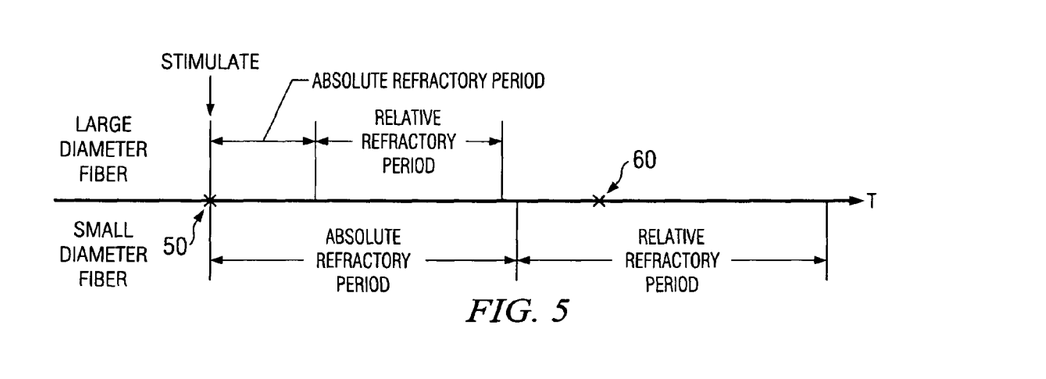
FIG. 5 illustrates an embodiment in which particular types of nerve fibers are targeted for refractory period adjustment.

FIG. 5 illustrates refractory periods for two different types of nerve fibers—large diameter fibers (e.g., A and B fibers) and small diameter fibers (e.g., C fibers). The refractory period for the small fiber type is longer than the refractory period of the large fiber type. In FIG. 5, it can be seen that it is possible to apply a second electrical signal to the nerve (comprising both fiber types) at a point in time (e.g., 60) that falls within the relative refractory period of the small diameter fibers, and yet falls outside the relative refractory period of the large diameter fibers. A second electrical signal applied at point 60 of an appropriate magnitude will extend the relative refractory period of the small diameter fibers. Because the second electrical signal occurs after the end of the relative refractory period of the large diameter fibers, it may still be used for stimulation of the large fibers. That is, the second electrical signal does not extend the relative refractory period of the large fibers (thereby allowing action potentials to occur) and does extend the relative refractory period in the small fibers (thereby precluding action potentials from occurring). As a result, the relative refractory period of selected fiber types can be extended. To the extent the fiber types whose relative refractory periods are selectively extended would otherwise cause various side effects, such side effects can be reduced or eliminated by keeping the selected fiber types in a relative refractory state.

Figure 6:
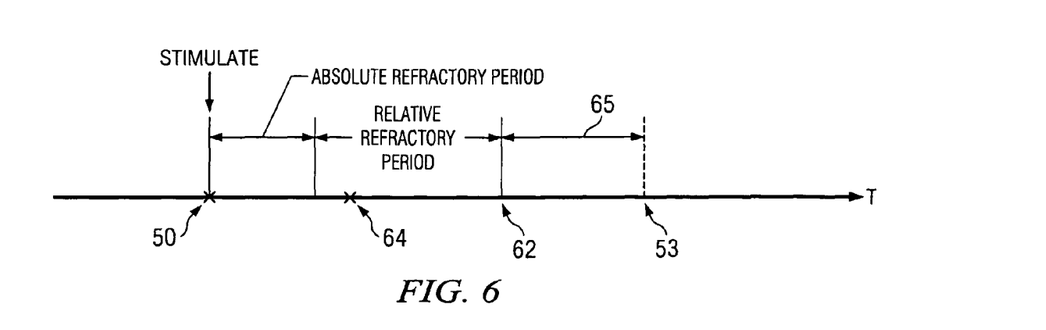
FIG. 6 illustrates an embodiment in which the refractory period is shortened via the application of an electrical signal with a different polarity than the polarity used to stimulate the nerve initially.

FIG. 6 illustrates the shortening of the intrinsic relative refractory period of a nerve via the application of a reverse polarity second electrical signal during the nerve's relative refractory period. A reverse polarity second electrical signal means that the current flows in the opposite direction than the direction of current flow in the first, therapeutic electrical signal applied at 50. As illustrated in FIG. 6, the end 53 of the nerve's intrinsic relative refractory period is shortened to 62 via the application of a reverse polarity current beginning at time 64 during the relative refractory period. The amount of time 65 by which the refractory period is shortened is a function of the magnitude and time duration of the reverse polarity second electrical signal.

Shortening the relative refractory period of a nerve causes the nerve to be available to be re-stimulated sooner than otherwise would be possible. As a result, therapies are possible in which the nerve can be stimulated a faster rate than without the use of the second electrical signal. Further, as illustrated in FIG. 5, some fiber types have longer refractory periods than other fiber types. By applying a reverse polarity current during the refractory period of the fiber types having the longer refractory periods (e.g., the small fiber types), the refractory periods of such fibers can be shortened and made substantially the same as, or at least closer to, the refractory periods of the fiber types having the intrinsically smaller relative refractory periods.

Figure 7:
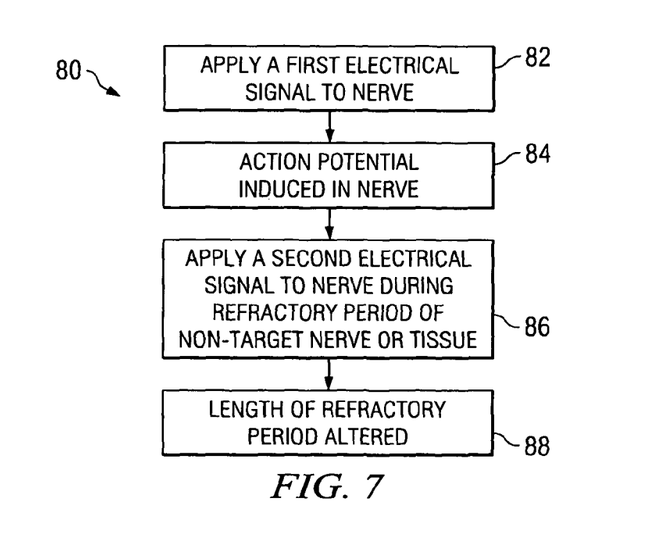
FIG. 7 illustrates a method of adjusting a refractory period of a nerve or other non-target tissue in accordance with a preferred embodiment of the invention.

FIG. 7 shows a method 80 of altering the refractory period of a nerve in accordance with an embodiment of the invention. At 82, method 80 comprises applying a first electrical signal in a nerve during a non-refractory period. The first electrical signal is selected to induce an action potential in the nerve, as shown at 84. Following the induced action potential, the method further comprises applying (step 86) a second electrical signal to the nerve during a refractory period of the non-target nerve/nerve fibers or non-target tissue. The second electrical signal alters the length of the refractory period (step 88). As discussed above, the alteration to the nerve's or non-target tissue's relative refractory period can be to extend or shorten the relative refractory period.

In accordance with at least some embodiments of the invention, the external programming system 20 (FIG. 1) can be used to program the IMD 10 to shorten or extend the nerve's or non-target tissue's relative refractory period. Via the programming system 20, one or more parameters are transmitted to the IMD 10 that cause the current generator 37 of the IMD 10 to provide an appropriate current to the nerve during the nerve's or non-target tissue's relative refractory period so as to shorten or lengthen the refractory period as desired.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

What is claimed is:

1. A method, comprising:
   applying a first electrical signal to a nerve to evoke an action potential, said nerve thereafter entering a refractory period in which said nerve is refractory to further induction of action potentials; and
   after applying said first electrical signal, altering said refractory period by applying a second electrical signal to said nerve during said refractory period, wherein said second electrical signal is effective to alter said refractory period and is unable to stimulate said nerve to evoke an action potential.

2. The method of claim 1 wherein applying said second electrical signal during said refractory period comprises providing current during a relative refractory period.

3. The method of claim 1 wherein applying said second electrical signal during said refractory period comprises providing current for a period of time that extends past said nerve's intrinsic refractory period.

4. The method of claim 1 wherein said refractory period comprises an absolute refractory period and a relative refractory period, and wherein applying said second electrical signal to said nerve during said refractory period comprises beginning to apply said second electrical signal to said nerve during said relative refractory period.

5. The method of claim 1 wherein altering said refractory period comprises shortening said refractory period by applying said second electrical signal having a polarity opposite that of a polarity of the first electrical signal.

6. The method of claim 1 wherein altering said refractory period comprises extending said refractory period by applying said second electrical signal having a polarity that is the same as a polarity of the first electrical signal.

7. The method of claim 1 wherein applying said second electrical signal to said nerve comprises applying said second electrical signal during a relative refractory period of a select nerve fiber type while not applying said second electrical signal during the refractory period of another nerve fiber type.

8. A method, comprising:
   applying a first electrical signal to a nerve to evoke an action potential;
   wherein said first electrical signal or said action potential evokes action potentials in non-target tissue;
   said non-target tissue thereafter entering a refractory period in which the nontarget tissue is refractory to further induction of action potentials; and
   after applying said first electrical signal, altering said refractory period of the non-target tissue by applying a second electrical signal to said nerve during said refractory period, wherein said second electrical signal is effective to alter said refractory period and has an insufficient magnitude to trigger an action potential in said non-target tissue.

9. The method of claim 8 wherein applying said second electrical signal during said refractory period comprises providing current during a relative refractory period.

10. The method of claim 8 wherein applying said second electrical signal during said refractory period comprises providing current for a period of time that extends past the non-target tissue's intrinsic refractory period.

11. The method of claim 8 wherein said refractory period comprises an absolute refractory period and a relative refractory period, and wherein applying said second electrical signal to said nerve during said refractory period comprises beginning to apply said second electrical signal to said nerve during said relative refractory period.

12. The method of claim 8 wherein altering said refractory period of the non-target tissue comprises shortening said refractory period by applying said second electrical signal having a polarity opposite that of a polarity of the first electrical signal.

13. The method of claim 8 wherein altering said refractory period of the non-target tissue comprises extending said refractory period by applying said second electrical signal having a polarity that is the same as a polarity of the first electrical signal.

14. The method of claim 8 wherein applying said second electrical signal to said nerve comprises applying said second electrical signal during a relative refractory period of a select nerve fiber type while not applying said second electrical signal during the refractory period of another nerve fiber type.

15. An implantable neurostimulator, comprising:
an electrical signal generator; and
an electrode coupled to said electrical signal generator and adapted to couple to a nerve;
wherein said electrical signal generator applies a first electrical signal to said nerve to evoke an action potential, said nerve thereby entering a refractory period in which said nerve is in a refractory state, and during said refractory period after applying said first electrical signal, said electrical signal generator alters said refractory period by applying a second electrical signal to said nerve, said second electrical signal being effective to alter said refractory period and unable to stimulate said nerve to evoke an action potential.

16. The implantable neurostimulator of claim 15 wherein said electrical signal generator extends said refractory period of said nerve.

17. The implantable neurostimulator of claim 15 wherein said electrical signal generator extends a relative refractory period of said nerve.

18. The implantable neurostimulator of claim 15 wherein said electrical signal generator shortens said refractory period of said nerve.

19. The implantable neurostimulator of claim 15 wherein said electrical signal generator shortens a relative refractory period of said nerve.

20. The implantable neurostimulator of claim 15 wherein said electrical signal generator applies said second electrical signal during a refractory period of a select nerve fiber type while not applying said second electrical signal during the refractory period of another nerve fiber type.

21. An implantable neurostimulator, comprising:
an electrical signal generator; and
an electrode coupled to said electrical signal generator and adapted to couple to a nerve to thereby provide therapy to a target nerve fiber;
wherein said electrical signal generator applies a first electrical signal to a nerve to evoke an action potential in the target nerve which causes an action potential to be evoked in a non-target nerve fiber or tissue, said non-target nerve fiber or tissue thereby entering a refractory period in which the non-target nerve fiber or tissue is in a refractory state, and during said refractory period after applying said first electrical signal, said electrical signal generator alters said refractory period of said non-target nerve fiber or tissue by applying a second electrical signal to said target nerve, said second electrical signal being effective to alter said refractory period and unable to trigger an action potential in said non-target nerve fiber or tissue.

22. The implantable neurostimulator of claim 21 wherein said first and second electrical signals have opposite polarities to each other and said refractory period is thereby shortened.

23. The implantable neurostimulator of claim 21 wherein said first and second electrical signals have a common polarity to each other and said refractory period is thereby extended.

* * * * *